United States Patent [19]

Kovacs

[11] Patent Number: 5,793,838
[45] Date of Patent: Aug. 11, 1998

[54] X-RAY EQUIPMENT

[76] Inventor: Sandor Kovacs, Furstenriederstr. 182, D-81377 Munich, Germany

[21] Appl. No.: 543,793

[22] Filed: Oct. 16, 1995

[30] Foreign Application Priority Data

| Oct. 17, 1994 | [DE] | Germany | 44 37 077.6 |
| Nov. 25, 1994 | [DE] | Germany | 44 41 974.0 |
| Dec. 28, 1994 | [DE] | Germany | 44 46 960.8 |

[51] Int. Cl.$^6$ ........................................ A61B 6/14
[52] U.S. Cl. .................... 378/39; 378/40; 378/98.8
[58] Field of Search ..................... 378/38, 39, 40, 378/41, 98.8, 146

[56] References Cited

U.S. PATENT DOCUMENTS

| 4,878,234 | 10/1989 | Pfeiffer et al. | 378/40 |
| 4,995,062 | 2/1991 | Schulze-Ganzlin et al. | 378/40 |
| 5,138,166 | 8/1992 | Makino et al. | 378/40 |
| 5,461,233 | 10/1995 | Yamamoto et al. | 378/40 |
| 5,550,380 | 8/1996 | Sugawara et al. | 250/370.09 |

*Primary Examiner*—Don Wong
*Attorney, Agent, or Firm*—Kirkpatrick & Lockhart LLP

[57] ABSTRACT

An X-ray equipment comprising an X-ray source and an imaging means detecting the X-rays passed through a subject for digital processing, whereby the imaging means may consist of an X-ray converter film and a sensor or of a storage film and a scanner. Such an X-ray equipment for the digital evaluation of X-rays can be used for panoramic images of a patient's jaw, for thorax images and images of other parts of the body. According to an embodiment of the present invention where an X-ray converter film and a sensor are used, the X-rays are incident on the X-ray converter film 13, which converts same into visible light. The light is passed to sensor 14 by an optical lens unit 18, said sensor being controlled and read by the signal processing unit 15a. The signal processing unit 15a separates, filters and intensifies the image signals and passes them on to the image storage card 16. The image storage card 16 is connected to PC 17, on the monitor of which the X-ray image can be shown and in which PC 17 said image may be permanently filed.

19 Claims, 3 Drawing Sheets

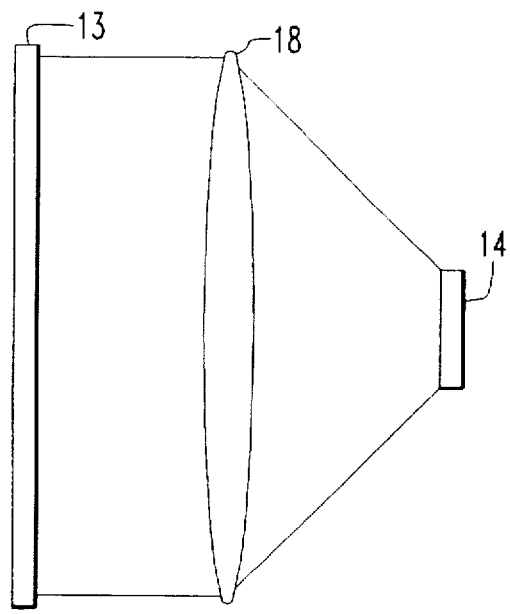
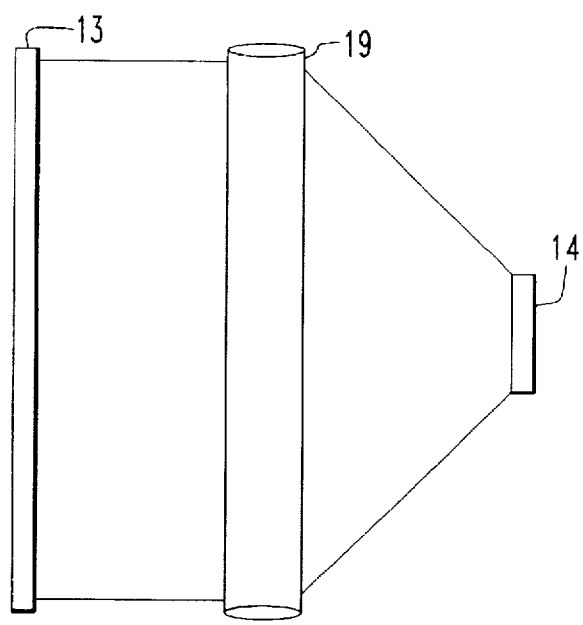
FIG. 4    FIG. 5
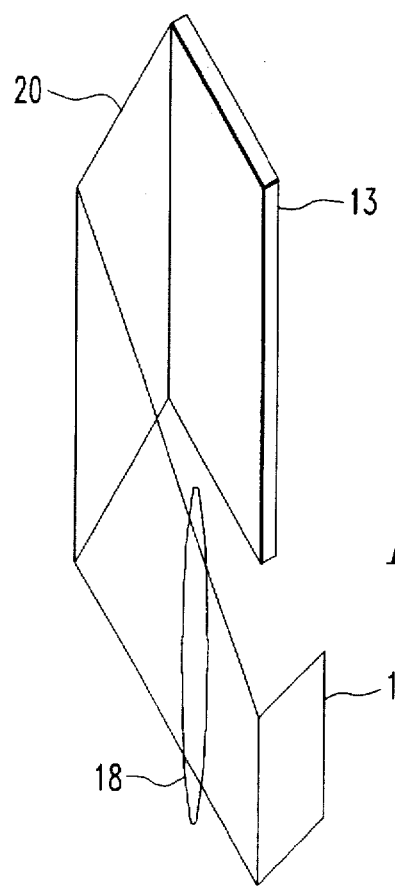
FIG. 6

X-RAY EQUIPMENT

BACKGROUND OF THE INVENTION

The invention relates to an X-ray equipment comprising an X-ray source and an imaging means, whereby the X-radiation detected by the imaging means is processed digitally without using an X-ray-sensitive film.

Such an X-ray equipment is known from EP 0 279 294. This known X-ray equipment is a dental X-ray diagnostics unit for providing panoramic tomographies of a patient's jaw. According to the said patent a pivotable arrangement is provided comprising a horizontal portion and two vertical portions, the horizontal portion being arranged above the patient's head and the two vertical portions being arranged diametrally opposed to each other on the sides of a patient's head. An X-ray source is accomodated in one vertical portion, said X-ray source being provided in a housing having a vertical slit in its side facing the head. In the other vertical portion an imaging means is provided. Here, the X-rays having passed through the head, are incident on a scintillator layer and are changed into visible light. The visible light is passed to a detector arrangement by means of glass fiber optics, said detector arrangement forming electric signals proportional to the intensity of radiation. To the detector arrangement there are added an analog to ditital converter, an image storage means and a data processing means with a computer, which computes a general image from the signals supplied by the detector arrangement during the taking of an X-ray.

With the known X-ray equipment, however, glass fiber optics are comparatively costly and therefore this equipment is relatively expensive.

SUMMARY OF THE INVENTION

An object of the present invention is to provide an X-ray equipment with the features of the opening paragraph of claim 1, which X-ray equipment does not suffer from said disadvantage.

Another object of the present invention is to provide an X-ray equipment with the features of the opening paragraph of claim 5, according to which defect sensors can be used which are very cheap.

The first object is solved for an X-ray equipment with the features of the opening paragraph of claim 1 by the feature of the characterizing portion of claim 1. The lens optics applied in this connection is much simpler and cheaper than the glass fiber optics used according to the prior art.

The second object for an X-ray equipment with the features of the opening paragraph of claim 5 is solved by the features of the characterizing portion of claim 5.

Due to the fact that several sensors are arranged in a row, only a fraction of the sensor area of an individual sensor has to work, such that cheap rejects or damaged goods can be used, which offers great advantages. The individual glass fiber optics for the sensors also are cheaper than one single bigger fiber optics for the entire system.

Further refinements of the inventions can be learnt from the subclaims.

Further objects, features and advantages of the teaching according to the present invention will be apparent from the following description thereof.

BRIEF DESCRIPTION OF THE DRAWINGS

FIG. 4 shows an X-ray converter film, a convex lens and a sensor according to another embodiment;

FIG. 5 shows an X-ray converter film, a cylindrical lens and a sensor according to still another embodiment, and FIG. 6 shows an X-ray converter film, a mirror, a convex lens and a sensor according to still another embodiment.

In FIG. 1 an X-ray equipment for providing panoramic images of a patient's jaw is shown—equipped with an X-ray film—as is used in many dental practices. According to the present invention either a sensor and an X-ray converter film or foil or a storage film or foil and a scanner are used instead of an X-ray film. At a support structure 6 a unit 9 is pivotably mounted. Unit 9 is provided with a horizontal portion and two vertical portions between which there is arranged the head of the patient. In one of the vertical portions a housing 4 is provided at the level of head 2, in which housing 4 an X-ray source 3 is provided, which according to the invention sends its rays through a vertical slit 5 arranged at the side of housing 4 facing head 2. At the other vertical portion of unit 9 there is provided, at the level of the head, the housing 8 of the imaging means 7, whereby the rays passing through the head are incident on the imaging means 7 through a vertical gap or slit provided in the housing 8. Unit 9 is slowly pivoted or rotated about the head 2 of the patient, the head 2 always being on the connecting line between the X-ray source and the imaging means. In this way gradually a panoramic image of a patient's jaw is produced. For a better adjustment of the head 2 of the patient there are provided a bite block (mouthpiece) 11 provided at a bite block bracket 18 attached to the support structure 6 as well as a nose-forehead-support 12 mounted at the support structure 6, too.

Figure 1:
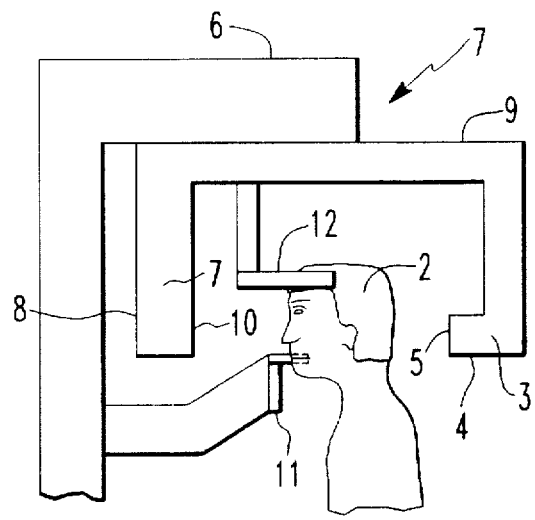
FIG. 1 is a side view of an X-ray equipment for producing panoramic images of a patient's jaw, and the patient's head.
Figure 1A:
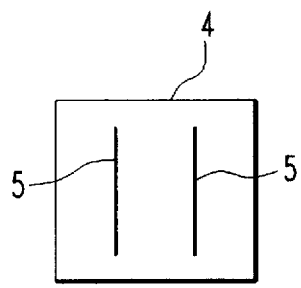
FIG. 1(a) is a front view of the housing of a preferred embodiment of the X-ray equipment showing two parallel vertical slits.

According to the present invention instead of one vertical gap or slit 5 two gaps or slits 5 extending in parallel may be provided as shown in FIG. 1(a), which are covered alternately by a covering means in such a manner that one gap or slit 5 isuncovered, respectively, and, in this way, this results in two X-ray images—taken one after the other—which are united to form one stereo image in a manner that is described in the following. According to a specific embodiment of the invention it is also possible to arrange a movable transverse gap or slit above gap or slit 5, which moves very quickly as regards its speed of rotation, such that this results in an imaging of slit 5 which is composed of various scan elements.

Figure 2:
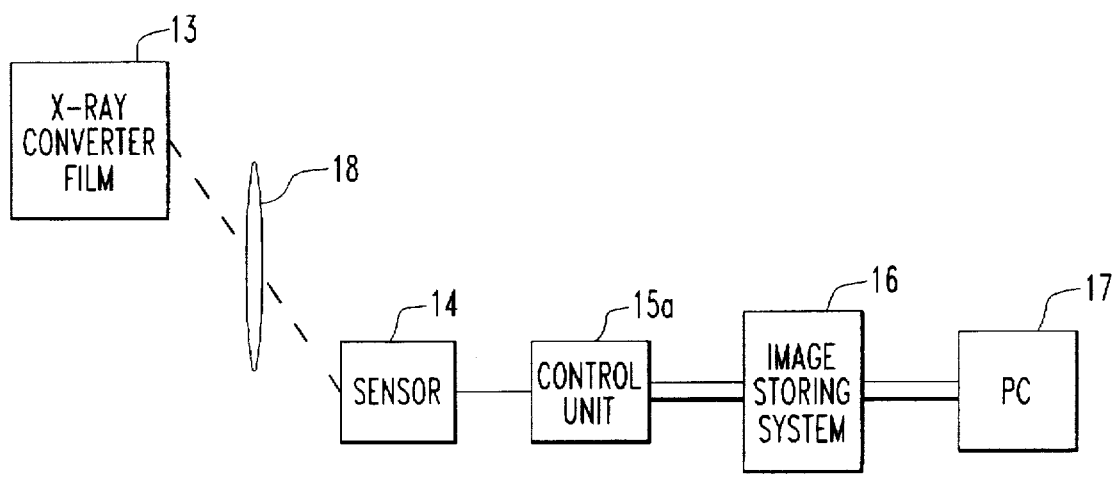
FIG. 2 is a block diagram showing an embodiment of the X-ray equipment according to the invention.

FIG. 2 shows a block diagram of an especially preferred embodiment of the present invention. The X-rays e.g. of an X-ray equipment for panoramic images of a jaw, are incident on the X-ray converter film 13 from the left side, which X-ray converter film 13 changes them into visible light. The visible light subsequently is passed via an optical lens unit 18 to a sensor 14 which takes a picture. The sensor 14 may be a line sensor or an area sensor (Flächensensor) with pixels distributed in the area. The line sensor may be a CCD (charge coupling device) or a spectroscopic high efficiency image sensor. Sensor 14 is controlled and "read" by the control unit 15a, whereby with a line sensor the driving or control is effected in the inverted mode. The specific construction of the spectroscopic high efficiency image sensor allows a high light constant by adding the light signals in a shift register. The time rate required for "reading" the line sensor is given by the control unit 15a. Control unit 15a which is also called a signal processing unit, separates, filters and intensifies or amplifies the signals arriving. Control unit 15a is provided with a filtering and intensifying or amplifying unit for filtering and amplifying. The information that can be utilized is then passed to an image storing card 16 by means of an internal bus system, said image storage card 16 being connected to a can be brought together and with a specific software personal computer (PC) 17. In PC 17 the image signals they can be shown on the monitor. The signals are sufficient for facilitating a diagnosis like with a film take. PC 17 is connected to an information system. In this information system the images are filed for documentary purposes in an electronic data bank or file, for instance in an opto-storage unit for a dentist's accounting system and can be printed at any time. According to the embodiment having two parallel gaps or slits 5, which are covered alternately by the covering means, the evaluation system given by block diagram 2 generates two differently colored images on the monitor of the PC 17, which images are off-set with respect to one another. If the viewer wears spectacles the glasses of which are colored in the respective color, he can see a stereo X-ray image.

According to the embodiment of the present invention where a movable transverse slit is moved across gap 5, the image shown on the monitor of the PC 17 is composed of the scanned portions of the respective gap image, whereby the gap images resulting from the slow rotating motion are again composed to form a total image.

According to the present invention not only X-ray equipment for taking panoramic images of a patient's jaw as shown in FIG. 1 is possible, but also X-ray equipment for all sorts of body parts such as e.g. images of the thorax or of the spinal column.

It is also possible to arrange the X-ray equipment according to the present invention as a computer tomograph.

Figure 3:
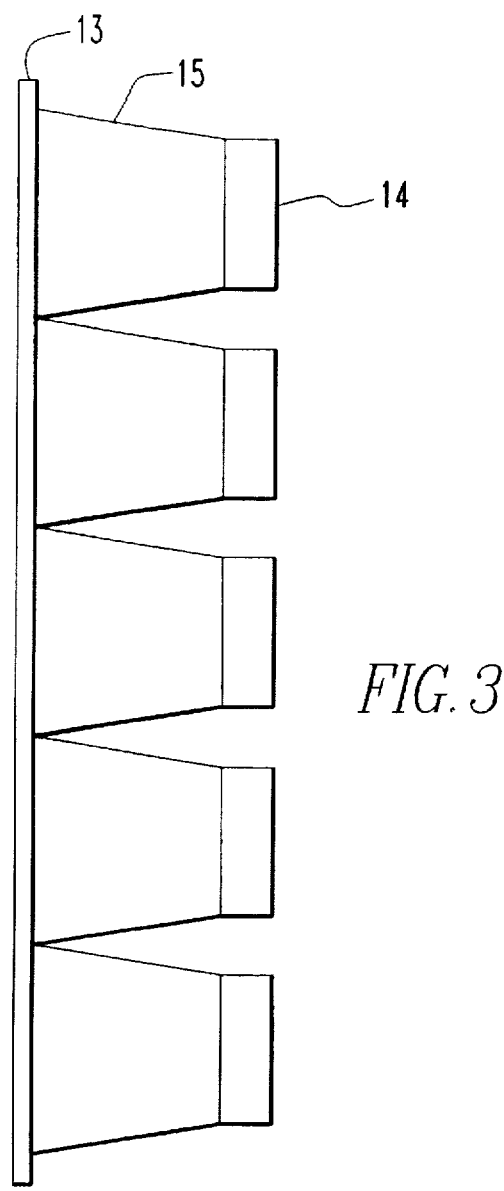
FIG. 3 shows an X-ray converter film, optical glass fiber units and sensors with respect to an embodiment where several sensors are used in a row.

FIG. 3 shows an embodiment according to which five sensors 14 are used arranged in a vertical row, to which sensors 14 the visible light from the X-ray converter film 13 is passed by means of five optical glass fiber units 15. According to this arrangement the optical glass fiber units 15 at the X-ray converter film 13 are directly adjacent to one another and extend towards the sensors 14 in a prism-shaped manner. With respect to this embodiment there are two advantages, namely on the one hand, that the five small optical glass fiber units 15 used are cheaper altogether than the bigger optical glass fiber unit according to the prior art and on the other hand, that a higher sensor capacity is provided which makes it possible to use sensors not operating a hundred per cent and, therefore, being rejects, they are very cheap. For instance, when using line sensors it is possible to make use of sensors with which only one fifth of the lines works.

In FIG. 4 an embodiment is shown according to which again only one sensor 14 is used. A convex lens 18 or a lens system 18 of convex lenses is used in order to pass the visible light from the X-ray converter film 13 to the sensor 14.

FIG. 5 corresponds to FIG. 4 with the only difference that in FIG. 5 a cylindrical lens 19 or a lens system 19 with cylindrical lenses is used.

According to FIG. 6 sensor 14 is arranged laterally of the X-ray converter film 13 and at a certain angle to the latter. Here, the light sent or radiated by the X-ray converter film 13 is deviated by a mirror 20, which is provided at a certain angle with respect to the X-ray converter film 13 and then is passed through a convex lens 18 to sensor 14. Instead of the mirror 20 also a prism can be used.

In general, also a light intensifier can be arranged between X-ray converter film 13 and sensor 14, in order to increase the sensitivity of the X-ray equipment.

What is claimed is:

1. An X-ray equipment comprising an X-ray source surrounded by a radiation-absorbing housing, said housing having at least one gap on a side facing a subject, an imaging means detecting the X-rays transmitted through the subject for digital processing, said imaging means being provided with an X-ray converter film for converting X-rays into lower frequency radiation, at least one sensor and an optical unit passing the lower frequency radiation from the converter film to the sensor, the X-ray source and the imaging means move along the subject to be X-rayed, such that a total image gradually results, a signal processing unit by which the sensor is controlled and read, an internal bus system, an image storage card, whereby the signals to be utilized are passed from the signal processing unit to the image storage card by the internal bus system, and a PC system coupled to an information system, whereby the image storage card is connected to the PC system and the X-ray is shown on the monitor of the PC system, characterized in that the optical unit is provided with at least one convex lens or cylindrical lens.

2. An X-ray equipment according to claim 1, wherein the X-ray converter film and the sensor are laterally displaced with respect to one another and the optical unit is extended by a prism or a mirror for deviating the lower frequency radiation.

3. An X-ray equipment comprising an X-ray source surrounded by a radiation-absorbing housing, said housing having a plurality of gaps on a side facing a subject, an imaging means detecting the X-rays transmitted through the subject for digital processing, said imaging means being provided with an X-ray converter film for converting X-rays into lower frequency radiation, a plurality of sensors and an optical unit passing the lower frequency radiation from the X-ray converter film to the sensors, the X-ray source and the imaging means move along the subject to be X-rayed such that a total image gradually results, a signal processing unit by which the sensors are controlled and read, an internal bus system, an image storage card, whereby the signals to be utilized are passed from the signal processing unit to the image storage card by the internal bus system and a PC system coupled to an information system, whereby the image storage card is connected to the PC system and the X-ray is shown on the monitor of the PC system, the sensors are arranged in a row in the X-ray source housing in parallel with the direction of the gap and the optical unit consists of a row of glass fiber units, whereby a glass fiber unit is associated to each sensor.

4. An X-ray equipment according to claim 3, wherein a light intensifier is arranged between the X-ray converter film and the optical unit.

5. An X-ray equipment according to claim 3, wherein an X-ray screening foil or film is arranged for protecting the sensors between the X-ray converter film or the sensor.

6. An X-ray equipment according to claim 3, wherein the glass fiber units of the X-ray converter film are directly adjacent to one another and extend towards said sensors in a prism-shaped manner, said sensors being arranged at a certain distance from one another.

7. An X-ray equipment according to claim 3, wherein the side of the X-ray source housing facing the subject to be X-rayed has two parallel gaps, for which covering means are provided, said covering means covering the gaps alternately in such a manner that one gap, respectively, remains uncovered or free and one image, respectively, of one gap appears on the monitor in a certain color, whereby two different colors correspond to the two gaps, such that a viewer wearing spectacles with two different glasses colored in the two different colors, can watch an X-ray stereo image.

8. An X-ray equipment according to claim 3, wherein above the gaps in the housing of the X-ray source a cover with a movable transverse gap is arranged, which moves rapidly with respect to the velocity of the X-ray source and the imaging means, such that the picture on the monitor is composed of the pictures of the gaps, which are composed of various scan elements.

9. An X-ray equipment according to claim 3, wherein the sensors are line sensors, the lines of which being arranged in parallel with the gaps in the X-ray source housing.

10. An X-ray equipment according to claim 3, wherein the sensors are area sensors having pixels distributed in the area.

11. An X-ray equipment according to claim 3, wherein the sensors are controlled by a signal processing unit in an inverted mode system.

12. An X-ray equipment according to claim 3, wherein the signals arriving in the signal processing unit are separated and filtered.

13. An X-ray equipment according to claim 12, wherein an intensifying or amplifying unit is provided in the signal processing unit and the separated and filtered signals are intensified or amplified by the intensifying unit.

14. An X-ray equipment according to claim 3, wherein the X-rays are stored by the PC system in an opto storage unit.

15. An X-ray equipment according to claim 14, wherein the X-rays are stored as a computer tomograph.

16. An X-ray equipment according to claim 3, wherein the X-ray equipment prepares panoramic images of a patient's jaw, said X-ray equipment having a support structure and a unit arranged at the support structure to be pivoted or rotated about the head, whereby in the unit the X-ray imaging unit is provided on one side of the head and on the other side of the head the X-ray source is provided.

17. An X-ray equipment according to claim 16, wherein the support structure has a bite block or mouthpiece and a nose-forehead support.

18. An X-ray equipment according to claim 3, wherein the gaps in the housing of the X-ray source are provided in the vertical direction.

19. An X-ray equipment according to claim 18, wherein the pivotable unit has a housing for the X-ray imaging unit and the housing at the side facing the head has a vertical gap.

* * * * *